US010119900B2

(12) United States Patent
Wang et al.

(10) Patent No.: US 10,119,900 B2
(45) Date of Patent: Nov. 6, 2018

(54) IN-LINE PARTICLE CHARACTERIZATION

(71) Applicant: New York University, New York, NY (US)

(72) Inventors: Chen Wang, Jersey City, NJ (US); Hagay Shpaisman, Kedium (IL); Andrew Hollingsworth, Princeton, NJ (US); David G. Grier, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/320,646

(22) PCT Filed: Jun. 24, 2015

(86) PCT No.: PCT/US2015/037472
§ 371 (c)(1),
(2) Date: Dec. 20, 2016

(87) PCT Pub. No.: WO2015/200512
PCT Pub. Date: Dec. 30, 2015

(65) Prior Publication Data
US 2017/0184485 A1    Jun. 29, 2017

Related U.S. Application Data

(60) Provisional application No. 62/017,008, filed on Jun. 25, 2014.

(51) Int. Cl.
*G06K 9/00* (2006.01)
*G01N 15/14* (2006.01)
(Continued)

(52) U.S. Cl.
CPC ..... *G01N 15/1463* (2013.01); *G01N 15/0211* (2013.01); *G02B 21/0004* (2013.01);
(Continued)

(58) Field of Classification Search
None
See application file for complete search history.

(56) References Cited

U.S. PATENT DOCUMENTS

| 4,627,729 A | 12/1986 | Breuckmann et al. |
| 2004/0004716 A1 | 1/2004 | Mavliev |

(Continued)

FOREIGN PATENT DOCUMENTS

WO    WO 2012/061752    5/2012

OTHER PUBLICATIONS

International Search Report and Written Opinion for Application No. PCT/US2015/037472, dated Sep. 23, 2015, 9 pages.
(Continued)

*Primary Examiner* — Atiba O Fitzpatrick
(74) *Attorney, Agent, or Firm* — Foley & Lardner LLP

(57) ABSTRACT

Holographic video microscopy yields fast and accurate measurements of the size and refractive index of individual colloidal particles. Particle-resolved characterization offers useful insights into the progress of colloidal synthesis without relying on models for the distributions of particle sizes and properties, and can be performed rapidly enough to provide feedback for process control. The measured increase in the most probable radius over the course of the reaction is consistent with the LaMer model for colloidal growth. Uniformity in the measured refractive index suggests that the spheres grow with uniform density. The joint distribution of size and refractive index provides evidence for a low rate of nucleation proceeding after the initial nucleation event. The same analysis reveals that these PDMS particles shrink by compactification in the first few days after their synthesis.

19 Claims, 4 Drawing Sheets

(51) Int. Cl.
*G02B 21/00* (2006.01)
*G01N 15/02* (2006.01)
*G03H 1/04* (2006.01)
*G03H 1/00* (2006.01)
*G03H 1/08* (2006.01)
*G06K 9/46* (2006.01)
*G06K 9/52* (2006.01)
*G06K 9/62* (2006.01)

(52) U.S. Cl.
CPC .......... *G03H 1/0005* (2013.01); *G03H 1/0443* (2013.01); *G03H 1/08* (2013.01); *G06K 9/0014* (2013.01); *G06K 9/00147* (2013.01); *G06K 9/4661* (2013.01); *G06K 9/52* (2013.01); *G06K 9/6212* (2013.01); *G03H 2001/005* (2013.01); *G03H 2001/0033* (2013.01); *G06K 2209/40* (2013.01)

(56) References Cited

U.S. PATENT DOCUMENTS

2006/0127369 A1\* 6/2006 Christensen ......... B01J 19/0046
424/93.7
2011/0043607 A1 2/2011 Grier et al.
2013/0308135 A1 11/2013 Dubois et al.

OTHER PUBLICATIONS

Hillman, T.R., et al., "Microscopic particle discrimination using spatially-resolved Fourier-holographic light scattering angular spectroscopy", Optics Express, Nov. 13, 2006, 14(23):11088-11102.
Examination Report in EP 16169799.0, dated Apr. 3, 2018, 4 pages.
Examination Report in EP 15811077.5, dated Apr. 12, 2018, 12 pages.

\* cited by examiner

Figure 1A-E

IN-LINE PARTICLE CHARACTERIZATION

CROSS REFERENCE TO RELATED APPLICATIONS

This application claims the benefit of U.S. Provisional Application No. 62/017,008 filed on Jun. 25, 2014, which is hereby incorporated by reference in its entirety.

STATEMENT OF GOVERNMENT INTEREST

This work was supported in part by the Materials Research Science and Engineering Program of the National Science Foundation through Grant No. DMR-0820341, the Federal Government may have certain rights in inventions described herein.

FIELD OF THE INVENTION

The present invention generally relates to the field of particle characterization. More specifically, the present invention relates to holographic techniques for particle characterization.

BACKGROUND OF THE INVENTION

Formation of materials such as colloidal have a wide range of applications. A variety of synthesis processes have been developed to create such particles. However, there is a need for characterization of such colloidal particles.

Holographic video microscopy has been applied to determine the properties of certain particles based upon application of Lorenz-Mie theory. However, there is a need for in-line and time-dependent changes in the particles both during synthesis and after synthesis is complete.

SUMMARY OF THE INVENTION

One embodiment of the invention relates to a method of characterizing of a plurality of particles. The method comprises generating a hologram based upon holographic video microscopy of a first particle of the plurality of particles at a first time. The refractive index and the radius of the first particle are determined at the first time. A hologram is generated based upon holographic video microscopy of a second particle of the plurality of particles at a second time. The refractive index and the radius of the second particle are determined at the second time.

Another embodiment relates to a method of characterizing a plurality of particles. Holograms of particles of the plurality of particles are generated, each hologram based upon holographic video microscopy of a particle $P_N$ of the plurality of particles at a different time $T_N$. The refractive index and the radius of the particle $P_N$ are determined at the time $T_N$. The change in the plurality of particles over time is characterized based upon the determined refractive index and radius of the particles.

Another embodiment relates to computer-implemented machine for characterizing a plurality of particles, comprising a processor; and a tangible computer-readable medium operatively connected to the processor and including computer code. The computer code is configured to: generate a hologram based upon holographic video microscopy of a first particle of the plurality of particles at a first time, determine the refractive index and the radius of the first particle at the first time, generate a hologram based upon holographic video microscopy of a second particle of the plurality of particles at a second time; and determine the refractive index and the radius of the second particle at the second time.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION OF THE PREFERRED EMBODIMENTS

Figure 1:
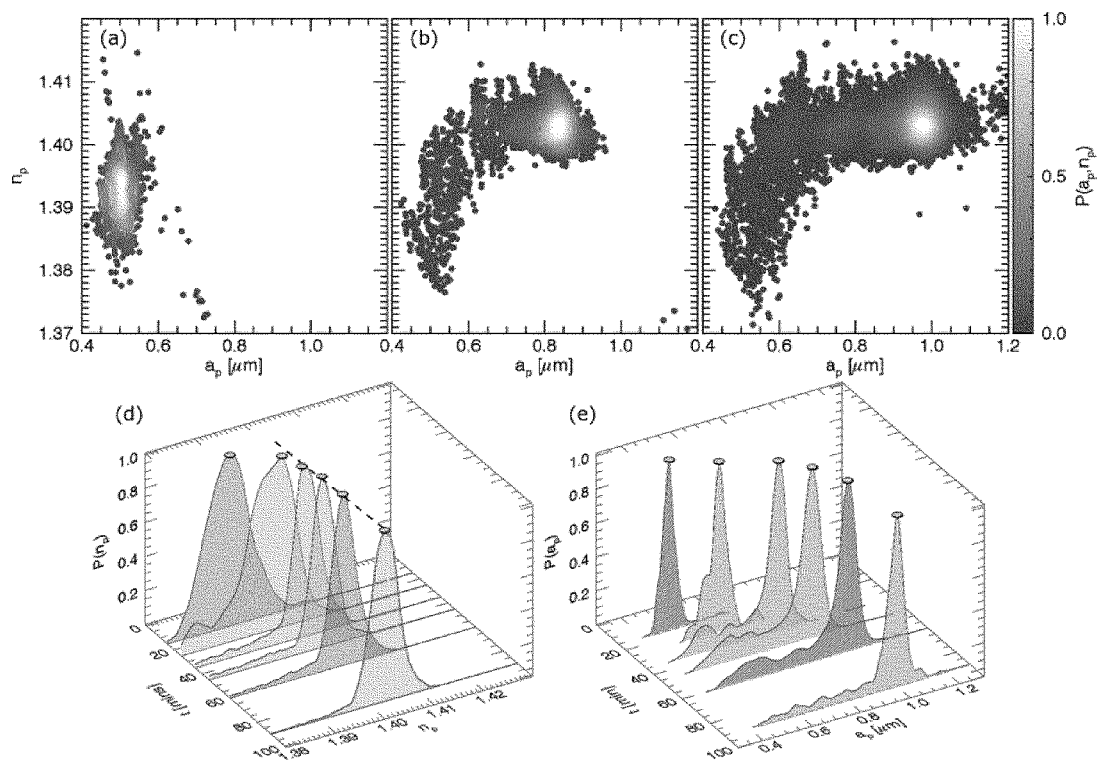
FIGS. 1A to 1C illustrate the distribution of particle radius and refractive index at (FIG. 1A) 15 min, (FIG. 1B) 35 min and (FIG. 1C) 60 min after initiation of polymerization, with the inset Inset: scanning electron micrograph of spheres obtained from another run of the same synthesis. Scale bar represents 2 mm. Each point represents the properties of one sphere and is colored according to the relative probability density P(ap, np). Each plot shows the properties of 5,000 randomly selected spheres.
FIG. 1D shows a graph of time evolution of the distribution of refractive indexes.
FIG. 1E shows a graph of time evolution of the distribution of particle radii.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Described herein are methods using Lorenz-Mie microscopy to characterize the time evolution of the radius and refractive indexes of colloidal spheres during the process of their synthesis. It also describes time-resolved measurements for these properties post synthesis.

Colloidal synthesis typically is monitored by performing time-resolved static light scattering, dynamic light scattering, or capillary hydrodynamic fractionation on samples removed from the reaction vessel. These measurements offer insights into the particles' size distribution at the time of sampling, typically by comparison to models for the anticipated distribution. Here, a general method is described for monitoring the progress of colloidal synthesis that uses holographic video microscopy to measure the radius and refractive index of individual particles. Distributions of properties compiled from such particle-resolved data reflect the true properties of the sample without a priori assumptions about the nature of the distributions. They therefore offer detailed insights into the mechanism of colloidal growth including the prevalence of secondary nucleation, the uniformity and reproducibility of the growth process, and the homogeneity and stability of the resulting particles. The capabilities of real-time holographic particle characterization by monitoring the synthesis of monodisperse samples of crosslinked polydimethysiloxane (PDMS) spheres are demonstrated below as an exemplary embodiment.

Holographic particle characterization uses predictions of the Lorenz-Mie theory of light scattering, to analyze holographic snapshots of individual spheres that are acquired with in-line holographic video microscopy. The scattering pattern due to an individual sphere is identified as a center of rotational symmetry and then fit pixel-by-pixel for the particle's three-dimensional position, its radius, and its refractive index. A typical hologram subtends a 200×200 pixel array. Each pixel has a relative noise figure of 0.009, as determined by the median-absolute-deviation (MAD) metric. Nonlinear least-squares fitting then yields the radius of a micrometer-scale sphere to within a nanometer and the refractive index with part-per-thousand precision, with a typical chi-squared characteristic of 1.2±0.5. This technique has been shown to work reliably for colloidal spheres ranging in radius from 400 nm to 4 µm.

One embodiment of a holographic microscope illuminates the sample with the collimated beam from a fiber-coupled diode laser operating at a vacuum wavelength of 447±1 nm (Coherent Cube). Light scattered by a sphere interferes with the rest of the beam in the focal plane of an objective lens (Nikon Plan Apo, 100×, numerical aperture 1.45, oil immersion). The magnified interference pattern is relayed with a tube lens to a video camera (NEC TI-324A), which records its intensity at 30 frames per second. This video stream then is digitized for analysis.

In one embodiment, colloidal samples flow through the microscope's 86 µm×65 µm field of view in a 2 cm×2 cm glass channel fabricated from a microscope slide and a number 1.5 cover slip, with a surface-to-surface separation of 15±5 µm. Results for spheres' radii and refractive indexes are found to be insensitive to axial position over the entire axial range.

To facilitate analysis, the colloidal dispersion is diluted to a volume fraction of 10-4 to minimize overlap of the spheres' holograms. In a preferred embodiment, the sample should be diluted to the point that the rings constituting neighboring particles' holographic images do not overlap. In one implementation, diluting to a volume fraction of $10^{-4}$ (expressed as a volume percentage: $10^{-2}$) is found to work well. Accurate determination of sample properties may also require additives to stabilize the sample for analysis. The diluent should have characterizable properties to allow for consideration of the impact of the diluent on the sample. In one embodiment, the diluent, moreover, must have a well-known refractive index at the laser's wavelength and at the temperature of the measurement, which can be checked with an Abbe refractometer. At a typical flow rate of 200 µm s-1 along the channel's midplane, data on several thousand spheres can be acquired in 5 min, thereby providing time-resolved information on the properties of the particles in the sample. Motion blurring does not appreciably affect the results under these conditions given the camera's 100 µs exposure time and the optical train's overall magnification of 135 nm per pixel.

Application to Growth of PDMS Spheres

Having access to real-time particle-resolved characterization data is useful for monitoring the progress of colloidal synthesis. To demonstrate this, holographic characterization is used to monitor the growth of monodisperse spheres of polydimethylsiloxane (PDMS) with varying degrees of crosslinking. The particles are synthesized by base-catalyzed hydrolysis and copolymerization of difunctional dimethyldiethoxysilane (DMDES) and trifunctional methyltriethoxysilane (MTES). A mixture of DMDES (Sigma-Aldrich, 1 vol %) and MTES (Sigma-Aldrich, 4 vol %) was added into water (Millipore MilliQ, 93 vol %) and 28-30 wt % ammonium hydroxide solution (ACROS Organics, 2 vol %) to obtain a total volume of 20 ml. The error for each volume measurement is less than 1 percent. The sample was shaken vigorously with a vortexer for 4 min at room temperature to initiate nucleation, and then left to polymerize on a rotating frame at 20 rpm for up to three hours.

a. Evolution of Size and Refractive Index During Growth

Starting from the initial mixing of silane monomer into the ammonia solution, 100 µl aliquots were taken from the reaction vessel at 15 min, 25 min, 35 min, 45 min, 60 min, and 90 min. Each aliquot was dispersed into 30 ml of 2 mM sodium dodecyl sulfate (SDS) solution (Sigma-Aldrich) to dilute the sample, thereby reducing the monomer concentration enough to stabilize the spheres. The error in sampling time is estimated to be 10 s. The diluted sample then is flowed through the holographic characterization system for analysis.

The data in FIG. 1A through FIG. 1C show the distribution of properties of spheres measured at 15 min, 35 min and 60 min. Each plot symbol represents the radius $a_p$ and refractive index $n_p$ of an individual sphere, and is comparable in size to the uncertainty in the estimated parameters. Symbols are colored by the joint probability density, $P(a_p, n_p)$, for observing particles with the specified properties, which is computed from the ensemble of single-particle measurements using a kernel density estimator.

The initial distribution in FIG. 1A is symmetric and quite sharply peaked in both size and refractive index, although particles smaller than the estimated 400 nm resolution limit of the technique would not have been resolved. The peak of the distribution, which incorporates 90% of the particles, sharpens as the reaction proceeds and moves to larger values of refractive index and radius. This can be seen in FIG. 1B and FIG. 1C. The range of refractive indexes becomes significantly smaller over the course of the reaction, which suggests that the particles in this principal population all develop to have comparable optical properties, and therefore comparable compositions. Holographic characterization is useful in this case for confirming the products' uniformity.

The data in FIG. 1D and FIG. 1E show the relative probabilities $P(n_p)$ and $P(a_p)$ for observing particles with refractive index $n_p$ and radius $a_p$ as a function of reaction time. Both distributions become increasingly sharp as the reaction progresses. The mode value for the refractive index varies little after 30 min, and is consistent with a value of $n_p = 1.401 \pm 0.002$.

The distribution $P(a_p)$ of particle radii plotted in FIG. 1E has a mode that increases with time for 60 min, and then remains constant. Indeed, the joint distribution $P(a_p, n_p)$ remains largely unchanged after the particles reach their maximum size. If the population of small particles arose from continuous nucleation events, the shape of $P(a_p, n_p)$ might be expected to change. Its constancy suggests that the small particles contributing to the long tail in $P(a_p)$ result from premature quenching of the polymerization reaction.

In addition to its principal peak, the distribution also develops a tail that traces out the reaction's history in the $(a_p, n_p)$ plane. This tail might arise because of secondary nucleation. Alternatively, it could reflect a population of particles that stopped growing before fully developing. Regardless of its origin, this secondary population constitutes a comparatively small proportion of the total number of particles, as quantified by the joint probability distribution, $P(a_p, n_p)$.

A small population of undersized spheres is evident in the scanning electron microscope image (Carl Zeiss MERLIN) inset into FIG. 1C. The most probable particle radius estimated from such images, 0.8 μm, is smaller than the mode radius of 0.93 μm obtained holographically for that batch of particles. This difference may reflect changes in the particles during drying and irradiation with the electron beam.

b. The Influence of Aging on Particle Properties

The distribution of size and refractive index does not change substantially between 60 min and 120 min, indicating that the reaction has run to completion. The particles' properties continue to develop, however, even after they are cleaned and resuspended in pure water. The data in FIG. 2 compare the results from FIG. 1A for the size and refractive index of spheres obtained at 15 min with an equivalent measurement made on the same batch of spheres T=16 day later. The diluted sample was kept sealed under ambient conditions for the intervening period. Over this period, the most probable radius decreased from $a_p(0)=0.50\pm0.01$ μm to $a_p(T)=0.48\pm0.01$ μm and the most probable refractive index increased from $n_p(0)=1.393\pm0.003$ to $n_p(T)=1.420\pm0.003$.

These changes may be accounted for by an increase in the density, $\rho_p(t)$, of the crosslinked PDMS. The refractive index depends on $\rho_p(t)$ through the Lorentz-Lorenz relation $$L(t) \equiv \frac{n_p^2(t) - 1}{n_p^2(t) + 2} = \frac{4}{3}\pi \rho_p(t) \alpha, \tag{1}$$

where α is the molecular polarizability at the imaging wavelength. Because $\rho_p(t)$ is a number density, the Lorentz-Lorenz factor, $L(t)$, is dimensionless. If the density scales inversely with the spheres' volume, then the density-scaled volume $$v(t) \equiv a_p^3(t) L(t) \tag{2}$$

should remain constant as the spheres shrink. The ratio $v(T)/v(0)=0.95\pm0.08$ indeed is consistent with unity. The observed evolution of particle properties thus is consistent with structural relaxation rather than chemical change.

Were shrinkage due to elimination of solvent from void-like pores over time, the distribution $P(a_p, n_p)$ initially would exhibit an anticorrelation that would decrease as the pores shrank. The absence of statistically significant correlations between $a_p$ and $n_p$ in either of the distributions plotted in FIG. 2 militates against this explanation. The observed shrinkage instead is better explained by densification through structural relaxation of the crosslinked polymer.

Figure 2:
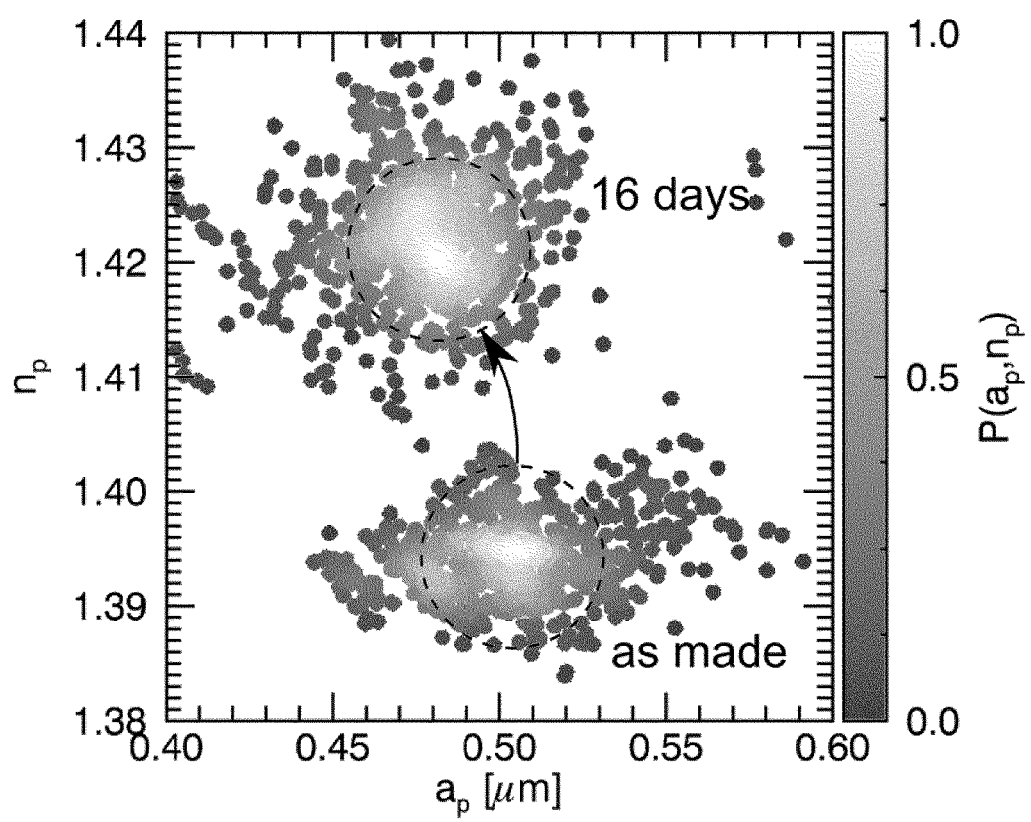
FIG. 2 shows the aging of PDMS particles from the sample in FIG. 1A extracted at 15 min. After 16 days, the mean radius has decreased and the mean refractive index has increased.

With this interpretation, the evolution of the most probable refractive index in FIG. 1 suggests that the primary nuclei are less dense than the final spheres. Whether the core density increases as the spheres grow or the cores become encased in higher-density shells cannot be determined from these data. Referring again to eqn (1), the spheres' effective density apparently changes by 2 percent over the course of the reaction.

c. Monitoring Colloidal Growth Kinetics

Figure 3:
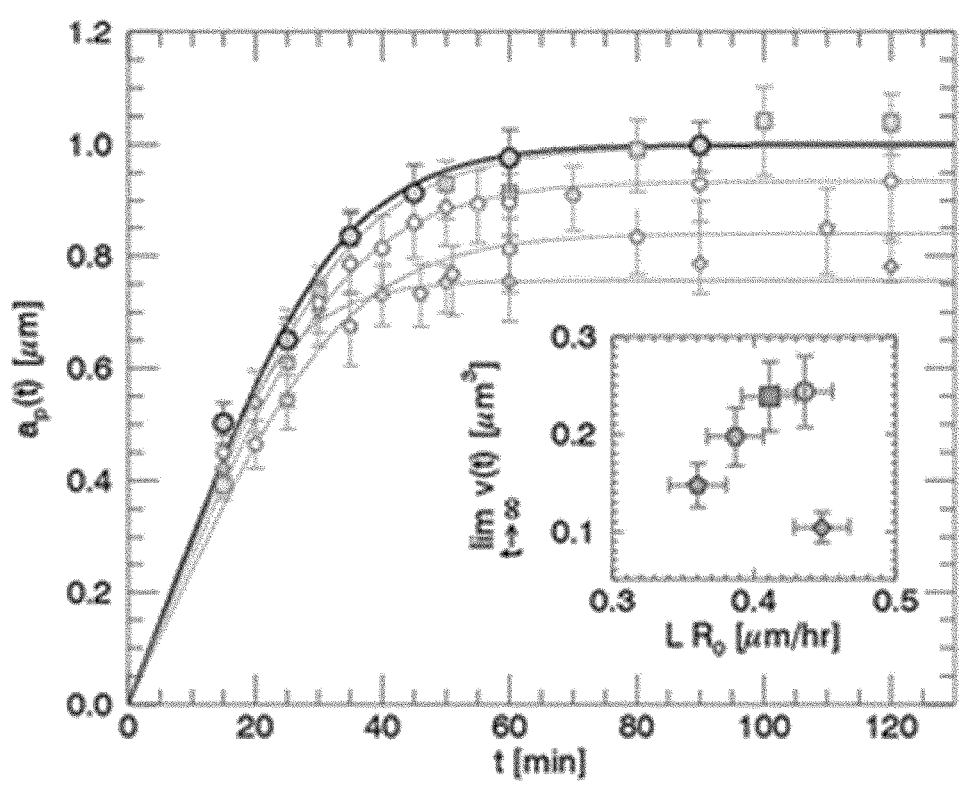
FIG. 3 illustrates the most probable radius as a function of time for five nominally identical batches of PDMS spheres at 80% crosslinker. The emphasized data set corresponds to the sample from FIG. 1E. Errors bars indicate the full width at half-maximum of the particle size distribution. Curves fit to equation 8. The inset portion shows distribution of particle volumes and growth rates obtained from the fits, scaled by Lorentz-Lorenz factors. The larger proportional range of scaled growth rates suggests that variations in nucleation efficiency account for variability in final particle size.

FIG. 3 shows how the most probable radius increased with time in the experiment from FIG. 1 and in other realizations of the same synthesis conducted under nominally identical conditions. Using conventional light-scattering techniques to obtain comparable data would have required the spheres' refractive index as an input parameter. Because $n_p(t)$ is found to depend on time, however, measurements would have suffered from systematic errors, particularly at early times.

These measurements are interpreted within the framework of the LaMer kinetic model for colloidal growth after rapid primary nucleation. This model assumes that each sphere grows independently in a volume V that is set by the number density of nuclei. As monomers are sequestered by the sphere, their number density in solution declines, $$\rho_m(t) \approx \rho_0 - \frac{4}{3}\pi a_p^3(t) \frac{1}{V} \rho_p. \tag{3}$$

For simplicity, the observed time dependence in $\rho_p(t)$ is neglected and it is assumed that $a_p^3(t)/V$ remains small. If, furthermore, the solution around the sphere remains well mixed, then the incoming flux of monomers at the sphere's surface, $$\Gamma(t) \approx \frac{D}{\delta} \rho_m(t), \tag{4}$$

is limited by diffusion across a thin boundary layer, where D is the monomers' diffusion coefficient and $\delta \ll V^{1/3}$ is the boundary layer's thickness. The sphere's radius then grows as $$\frac{da_p}{dt} = R_0[1 - \kappa^3 a_p^3(t)], \tag{5}$$

where the initial growth rate is $$R_0 = \Gamma(0) \rho_p^{-1}, \tag{6}$$

and where $$\kappa = \left(\frac{4\pi}{3} \frac{\rho_p}{\rho_0} \frac{1}{V}\right)^{1/3} \tag{7}$$

is related to the asymptotic radius by $\kappa^{-1}=\lim_{t\to\infty} a_p(t)$. Eqn (5) yields an implicit formula for $a_p(t)$, $$\kappa R_0(t-t_0) = \frac{1}{6}\ln\left(1 + \frac{3\kappa a_p(t)}{[1-\kappa a_p(t)]^2}\right) + \frac{1}{\sqrt{3}}\tan^{-1}\left(\frac{\sqrt{3}\,\kappa a_p(t)}{2+\kappa a_p(t)}\right), \quad (8)$$

where $t_0$ is the time required for primary nucleation. It is assumed that $t_0$ is small enough to be neglected. Curves in FIG. 3 are fits of eqn (8) to data from five nominally identical realizations of the same synthetic protocol, including the sample from FIG. 1, with $R_0$ and $\kappa$ as adjustable parameters.

Tracking both size and refractive index offers insights into the growth mechanism that cannot be obtained with conventional characterization methods. For example, the variability in particle size evident in FIG. 3, might be due to differences in the density of the growing microgel. Alternatively, it might reflect differences in number of primary nuclei. Holographic characterization offers insights that can distinguish these scenarios.

All five runs were performed with the same initial monomer concentration, $\rho_0$, at the same temperature, and with the same mixing protocol. The five runs all have values of L obtained from refractive index data that are consistent with 0.243±0.003. The small range suggests that the microgel grew with consistent density in all five samples. Using the Lorentz-Lorenz factor $L(t)$ as a proxy for the spheres' density, the scaled growth rate, $L(t)R_0=4/3\pi\alpha\Gamma(0)$, similarly should not vary appreciably between runs. Indeed, values of $L(t)R_0$ plotted in the inset to FIG. 3 vary by 10 percent relative to the mean. These observations suggest that post-nucleation growth conditions were consistent from run to run.

The asymptotic value of the normalized volume $\lim_{t\to\infty} v(t)=\kappa^{-3}L=\alpha\rho_0 V$, offers insight into the nucleation process through the number density of primary nuclei, $V^{-1}$. Values of $\lim_{t\to\infty} v(t)$ plotted in the inset to FIG. 3 vary by nearly 50 percent relative to the mean. The run-to-run variation, moreover, is substantially larger than the single-run uncertainty. Taken together, the comparative consistency of $L(t)R_0$ and the relative variability of $\lim_{t\to\infty} v(t)$ suggest that inconsistency in the products' mean size may be ascribed to variations in the number of primary nuclei, and that efforts to improve reproducibility therefore should focus on the initial mixing process.

CONCLUSIONS

These results demonstrate that holographic characterization can be used to monitor the properties of colloidal particles both in-line as the reaction proceeds, and also after synthesis is complete to gauge stability. Although the present discussion focuses on a particular system for illustrative purposes, the same method also can be used to monitor other types of colloidal spheres synthesized by other routes, including emulsion polymerization, dispersion polymerization, and sol-gel precipitation. Holographic characterization can be performed in real time using hardware-accelerated fitting or through machine-learning methods. The resulting time-resolved data on the particle-size distribution is suitable for existing real-time process control systems. By providing independent measurements of individual particles' sizes and refractive indexes, moreover, holographic characterization offers insights into the mechanisms of growth and aging that cannot be obtained with conventional characterization techniques. These data streams create new opportunities for in-line process control and quality assurance. The wealth of precise time-resolved data offered by holographic characterization, together with its low cost and ease of implementation also recommend its adoption for laboratory-scale applications.

Real-time in-line monitoring of colloidal properties can be used to demonstrate compliance with regulations regarding the size distribution and composition of colloidal materials. It also can be used to assess and verify the quality of colloidal materials being used as inputs to other processing steps such as compounding into pharmaceuticals, mixing into foods, and blending into cosmetics and other consumer products. It should be appreciated by one of skill in the art that there are uses for pre-, intra- and post-process holographic characterization.

Figure 4:
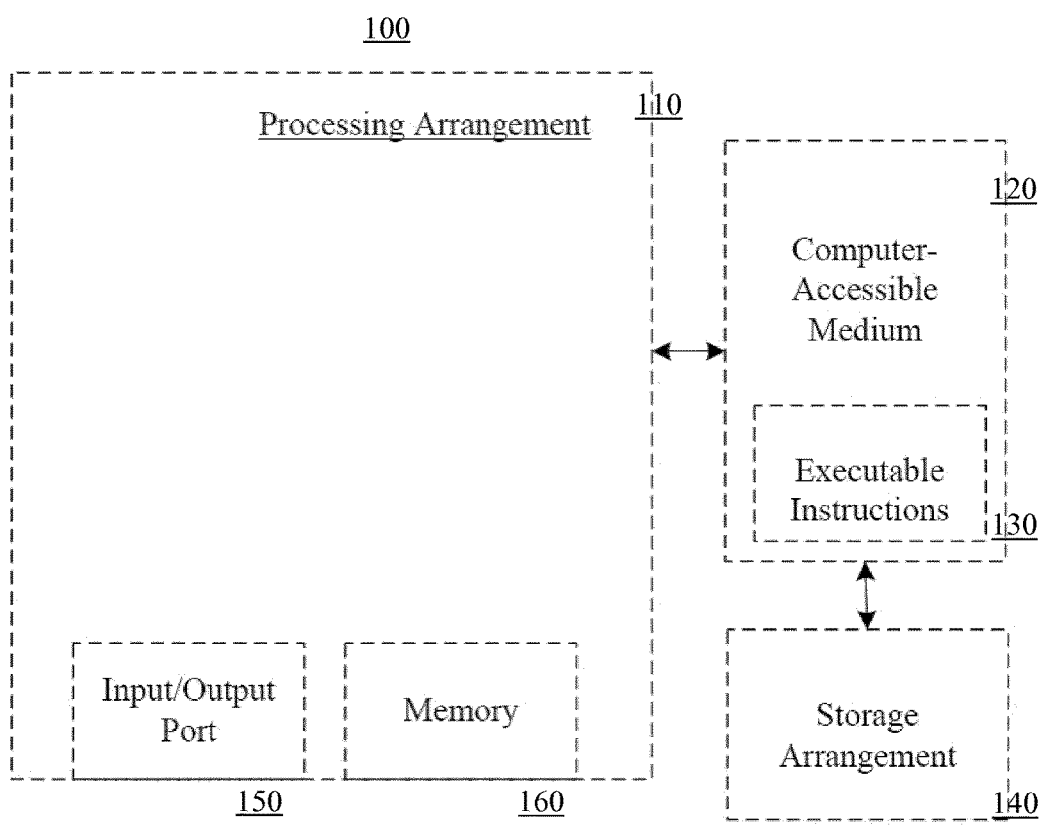
FIG. 4 shows a computerized implementation of the invention.

As shown in FIG. 4, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). Methods and systems of the present invention may be implemented with a computer in whole or in part. For example, computerized control of the holographic video microscopy system may be utilized and/or the determinations regarding The computer-accessible medium 120 may be a non-transitory computer-accessible medium. The computer-accessible medium 120 can contain executable instructions 130 thereon. In addition or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method of characterizing a plurality of particles, comprising:
    flowing the plurality of particles through a field of view of a holographic video microscopy system;
    generating a hologram based upon holographic video microscopy of a first particle of the plurality of particles, which is within the field of view at a first time;
    determining the refractive index, density, and the radius of the first particle at the first time;
    generating a hologram based upon holographic video microscopy of a second particle of the plurality of particles, which is within the field of view at a second time; and
    determining the refractive index, density, and the radius of the second particle at the second time.

2. The method of claim 1, further comprising monitoring synthesis of the plurality of particles based upon comparison of the first particle refractive index and radius and the second particle refractive index and radius.

3. The method of claim 1, further comprising, wherein the first time and second time are after synthesis of the plurality of particles, monitoring post-synthesis stability of the plurality of particles.

4. The method of claim 1 wherein determining the refractive index and the radius comprises application of Lorenz-Mie theory.

5. The method of claim 1, further comprising determining whether synthesis of the plurality of particles has concluded.

6. The method of claim 1 further comprising a flow rate of about 50 µm/s.

7. The method of claim 1, wherein determining the refractive index and the radius of the first particle and determining the refractive index and the radius of the second particle comprise determining a probability density for refractive index and radius for the first particle and determining a probability density for refractive index and radius for the second particle, respectively.

8. A method of characterizing a plurality of particles, comprising generating holograms of particles of the plurality of particles, each hologram based upon holographic video microscopy of a particle $P_N$ of the plurality of particles at a different time T; and
    determining a time $T_N$ refractive index and a time $T_N$ radius of the particle $P_N$ at a time $T_N$;
    determining a time $T_{N+1}$ refractive index and a time $T_{N+1}$ radius of the particle $P_N$ at a time $T_{N+1}$;
    characterizing a change in the plurality of particles over time based upon a comparison of the time $T_N$ refractive index and the time $T_{N+1}$ refractive index and the time $T_N$ radius and the time $T_{N+1}$ radius;
    determining if the change in the plurality of particles is a chemical change or a structural change.

9. The method of claim 8, further comprising monitoring synthesis of the plurality of particles based upon comparison of the determined refractive indices and radii.

10. The method of claim 8, further comprising, wherein the holograms are generated after synthesis of the plurality of particles, monitoring postsynthesis stability of the plurality of particles.

11. The method of claim 8 wherein determining the refractive index and the radius comprises application of Lorenz-Mie theory.

12. The method of claim 8, further comprising flowing the plurality of particles through a holographic video microscopy system.

13. The method of claim 12 further comprising a flow rate of about 50 µm/s.

14. The method of claim 8, wherein determining the refractive index and the radius of the first particle and determining the refractive index and the radius of the second particle comprise determining a probability density for refractive index and radius for the first particle and determining a probability density for refractive index and radius for the second particle, respectively.

15. A computer-implemented machine for characterizing a plurality of particles, comprising:
    a processor; and
    a tangible computer-readable medium operatively connected to the processor and including computer code configured to:
        generate a hologram based upon holographic video microscopy of a first particle of the plurality of particles, the first particle flowing through a field of view of a holographic video microscopy system, at a first time; and
        determine the refractive index and the radius of the first particle at the first time;
        generate a hologram based upon holographic video microscopy of a second particle of the plurality of particles at a second time; and
        determine the refractive index and the radius of the second particle at the second time.

16. The computer-implemented machine of claim 15, further comprising computer code configured to monitor synthesis of the plurality of particles based upon comparison of the first particle refractive index and radius and the second particle refractive index and radius.

17. The method of claim 15, further comprising computer code configured to monitor, wherein the first time and second time are after synthesis of the plurality of particles, post-synthesis stability of the plurality of particles.

18. The method of claim 1, wherein, prior to generating a hologram, a colloidal suspension of the plurality of particles is diluted to a volume faction of at least $10^{-4}$.

19. The method of claim 8, wherein determining if the change is a chemical change or a structural change, further comprises determining density of the plurality of particles.

\* \* \* \* \*